US008167952B2

(12) United States Patent
Graham et al.

(10) Patent No.: US 8,167,952 B2
(45) Date of Patent: May 1, 2012

(54) ARTHROPLASTIC IMPLANT WITH SHIELD FOR BASILAR JOINT AND RELATED METHODS

(75) Inventors: Thomas James Graham, Timonium, MD (US); H. Brent Bamberger Do, Kettering, OH (US); James Howard Calandruccio, Memphis, TN (US); Thomas A. Wiedrich, Wilmette, IL (US); Louise M. Focht, Del Mar, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 188 days.

(21) Appl. No.: 12/203,233

(22) Filed: Sep. 3, 2008

(65) Prior Publication Data
US 2010/0057213 A1    Mar. 4, 2010

(51) Int. Cl.
*A61F 2/42* (2006.01)
(52) U.S. Cl. .................... 623/21.15; 623/21.11
(58) Field of Classification Search .... 623/21.11–21.14, 623/21.15; 606/906, 902, 280
See application file for complete search history.

(56) References Cited

U.S. PATENT DOCUMENTS

| 4,164,793 | A  | 8/1979  | Swanson ................ 3/1.91 |
| 4,198,712 | A  | 4/1980  | Swanson ................ 3/1.91 |
| 4,936,860 | A  | 6/1990  | Swanson ................ 623/21 |
| 4,969,908 | A  | 11/1990 | Swanson ................ 623/21 |
| 5,314,485 | A  | 5/1994  | Judet ................... 623/21 |
| 5,326,364 | A  | 7/1994  | Clift, Jr. et al. .......... 623/21 |
| 5,360,431 | A  | 11/1994 | Puno et al. .............. 606/72 |
| 5,645,605 | A  | 7/1997  | Klawitter ............... 623/21 |
| 5,827,285 | A  | 10/1998 | Bramlet ................. 606/60 |
| 5,984,926 | A  | 11/1999 | Jones ................... 606/72 |
| 5,984,970 | A  | 11/1999 | Bramlet ................ 623/21 |
| 6,221,074 | B1 | 4/2001  | Cole et al. .............. 606/62 |
| 6,283,969 | B1 | 9/2001  | Grusin et al. ............ 606/69 |
| 6,302,887 | B1 | 10/2001 | Spranza et al. ........... 606/73 |
| 6,440,135 | B2 | 8/2002  | Orbay et al. ............. 606/69 |
| 6,475,242 | B1 | 11/2002 | Bramlet .............. 623/21.11 |
| 6,565,960 | B2 | 5/2003  | Koob et al. ............. 428/304.4 |
| 6,699,292 | B2 | 3/2004  | Ogilvie et al. .......... 623/21.15 |
| 6,821,530 | B2 | 11/2004 | Koob et al. ............. 424/458 |
| 7,090,676 | B2 | 8/2006  | Huebner et al. ........... 606/71 |

(Continued)

FOREIGN PATENT DOCUMENTS

WO    96/03084    2/1996

(Continued)

OTHER PUBLICATIONS

TONIER US, Medical Professionals, Wrist Products, CoverLoc Volar Plate, 2008.

(Continued)

*Primary Examiner* — David H Willse
*Assistant Examiner* — Tiffany Shipmon
(74) *Attorney, Agent, or Firm* — Tarolli, Sundheim, Covell & Tummino LLP

(57) ABSTRACT

An arthroplastic implant for a basilar joint of a hand of a patient includes a body having a distal surface and a proximal surface opposite therefrom. The distal surface is to be positioned adjacent a first metacarpal bone at the basilar joint of the hand of the patient. The arthroplastic implant also includes a shield extending outwardly from the distal surface of the body to shield adjacent portions of the first metacarpal bone and a second metacarpal bone of the hand of the patient.

32 Claims, 4 Drawing Sheets

U.S. PATENT DOCUMENTS

| | | | |
|---|---|---|---|
| 7,189,237 B2 | 3/2007 | Huebner | 606/69 |
| 7,326,212 B2 | 2/2008 | Huebner | 606/69 |
| 2003/0216813 A1* | 11/2003 | Ball et al. | 623/21.12 |
| 2004/0138754 A1 | 7/2004 | Lang et al. | 623/20.14 |
| 2004/0158251 A1 | 8/2004 | Morrison et al. | 606/71 |
| 2005/0049710 A1 | 3/2005 | O'Driscoll et al. | 623/20.11 |
| 2005/0070902 A1 | 3/2005 | Medoff | 606/62 |
| 2005/0216090 A1 | 9/2005 | O'Driscoll et al. | 623/20.32 |
| 2005/0234458 A1 | 10/2005 | Huebner | 606/69 |
| 2005/0245931 A1 | 11/2005 | Orbay | 606/69 |
| 2006/0015101 A1 | 1/2006 | Warburton et al. | 606/62 |
| 2006/0052725 A1* | 3/2006 | Santilli | 600/587 |
| 2006/0089648 A1 | 4/2006 | Masini | 606/69 |
| 2006/0100715 A1* | 5/2006 | De Villiers | 623/23.4 |
| 2006/0155284 A1 | 7/2006 | Doherty | 606/69 |
| 2006/0173458 A1 | 8/2006 | Forstein et al. | 606/69 |
| 2007/0014649 A1 | 1/2007 | James | 411/81 |
| 2007/0043357 A1 | 2/2007 | Kirschman | 606/61 |
| 2007/0083202 A1 | 4/2007 | Running et al. | 606/62 |
| 2007/0123867 A1 | 5/2007 | Kirschman | 606/61 |
| 2007/0173834 A1 | 7/2007 | Thakkar | 606/62 |
| 2007/0173841 A1 | 7/2007 | Ralph et al. | 606/69 |
| 2007/0265629 A1 | 11/2007 | Martin et al. | 606/69 |

FOREIGN PATENT DOCUMENTS

WO 01/24717 4/2001

OTHER PUBLICATIONS

SBI Small Bone Innovations, SCS ™ Volar Distal Radius Plate Sytem, Surgical Technique, 2006, pp. 1-9.

SBI Small Bone Innovations, SCS™ Volar Distal Radius Plate, 2008.

* cited by examiner

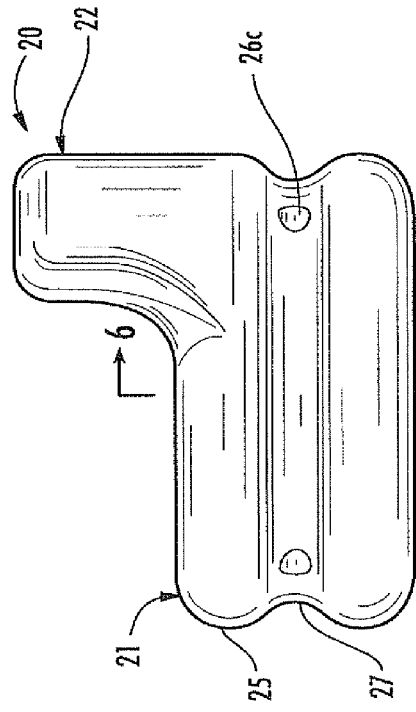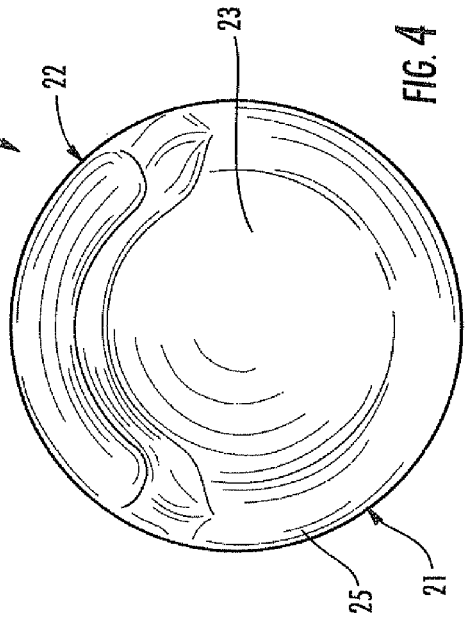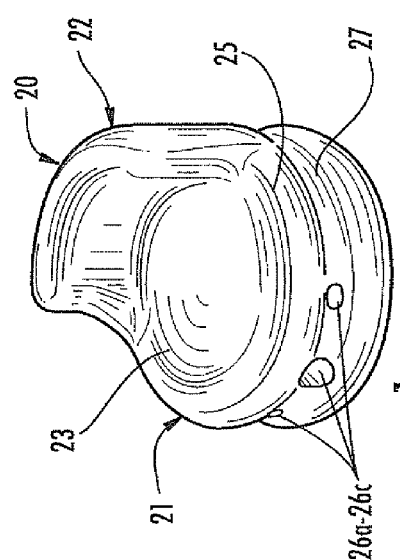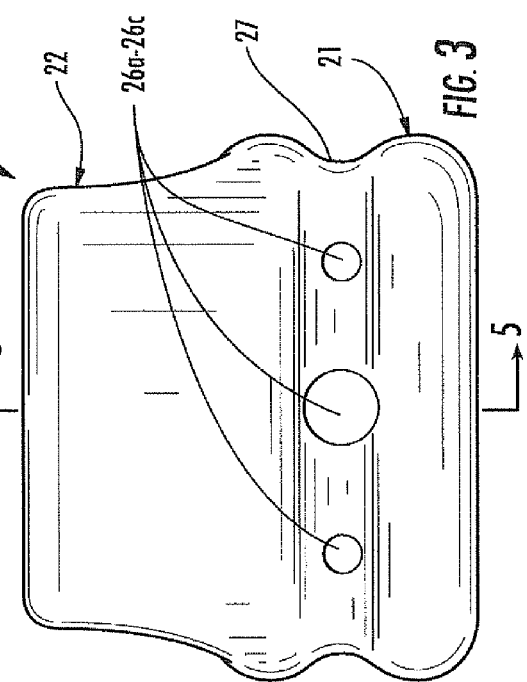
FIG. 2
FIG. 4
FIG. 3
FIG. 1

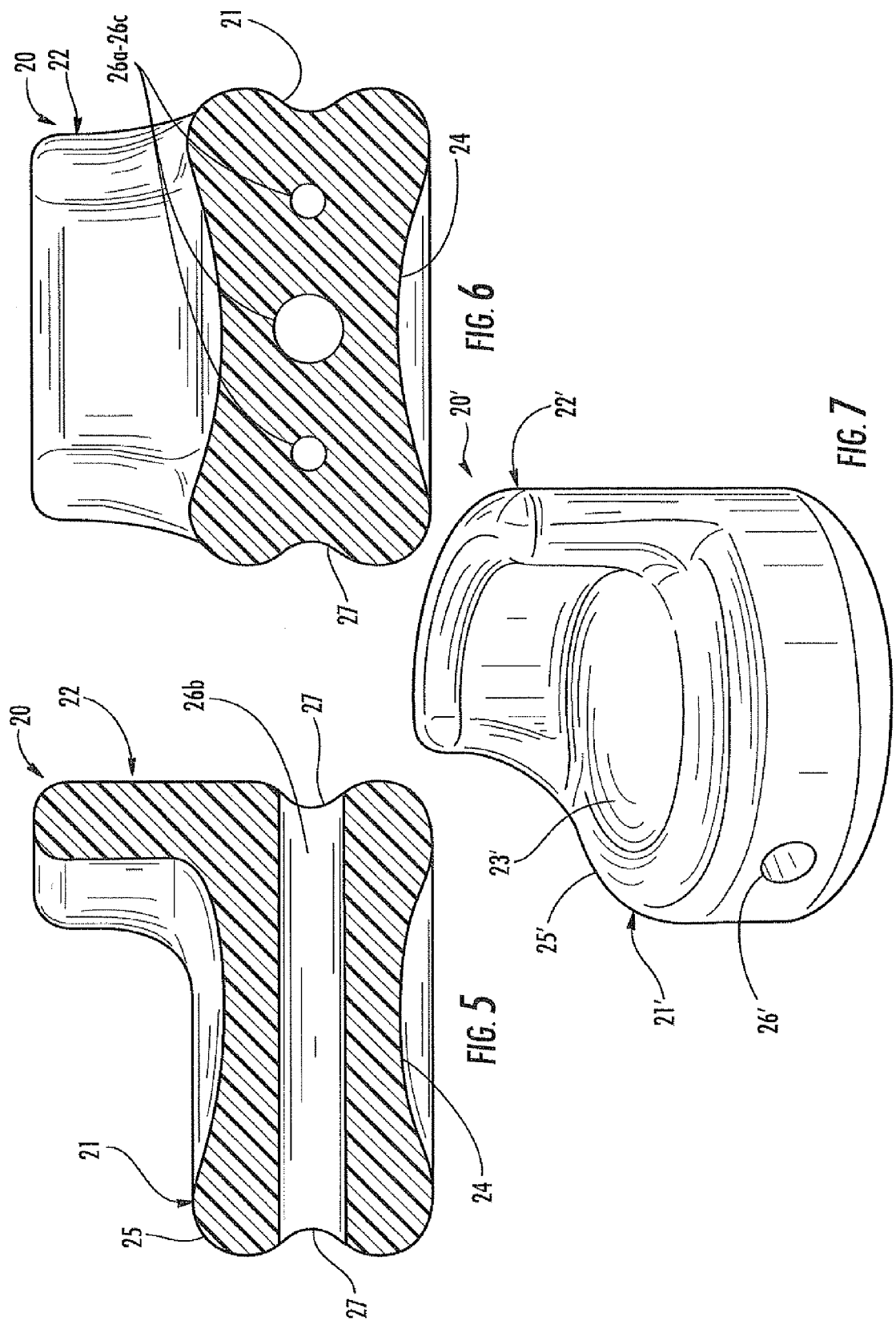

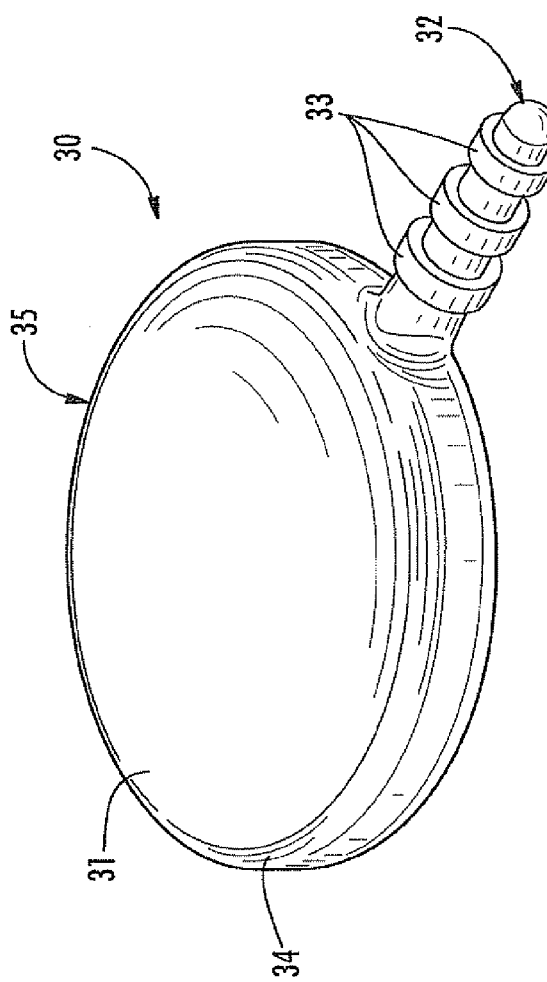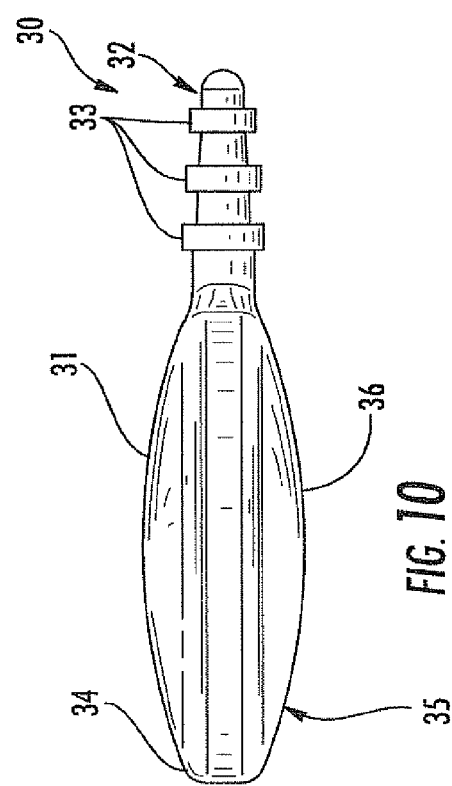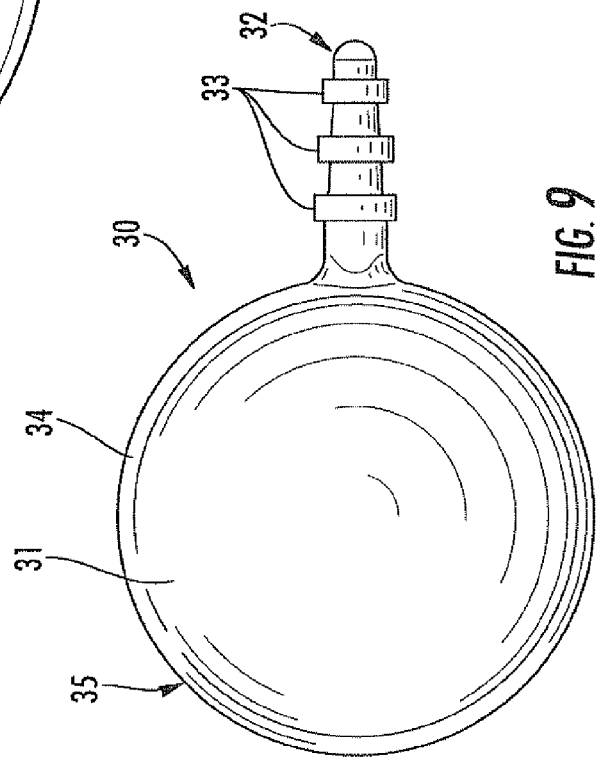
FIG. 8
FIG. 9
FIG. 10

ARTHROPLASTIC IMPLANT WITH SHIELD FOR BASILAR JOINT AND RELATED METHODS

FIELD OF THE INVENTION

The present invention relates to the field of arthroplastic implants, and, more particularly, to arthroplastic implants for treating disorders of the basilar or carpometacarpal (CMC) joint and related methods.

BACKGROUND OF THE INVENTION

The clinical syndrome of Osteoarthritis, which is also known as degenerative arthritis or degenerative joint disease, is characterized by a loss of articular cartilage on adjacent bony surfaces resulting in discomfort, loss of motion, and functional impairment. In a similar fashion, inflammatory arthritis, for example, rheumatoid arthritis, may result in a loss of cartilage surfaces from both biochemical and mechanical reasons. Furthermore, an accelerated loss of cartilage can result from traumatic injury to bones and joints and promote posttraumatic arthritis. As the bony surfaces become less protected by cartilage, the patient experiences pain, motion limitation, potential joint instability, and eventual functional impairment. Due to a decreased movement resulting from the pain or joint changes, regional muscles may atrophy, and ligaments may become more lax. Osteoarthritis is the most common form of arthritis, but inflammatory and post-traumatic arthritis also affect millions of patients.

Arthritis of the carpometacarpal (CMC) joint or "basilar" joint of the thumb is the development of pathologic changes of the articular cartilage and surrounding bone at a patient's joint involving, but not limited to, the relationship between the thumb metacarpal and the trapezium (one of the carpal or wrist bones). The effects of basilar joint arthritis may include, for example, debilitating hand pain, swelling, and decreased strength and range of motion, making it difficult to do simple tasks. Further pathologic involvement of bones local to the trapezium bone is often seen in this syndrome. As with the other articular relationships of the trapezium bone, those with the scaphoid and trapezoid bones (other carpal or wrist bones) may also manifest similar pathologic changes of the articular cartilage and surrounding bone due to basilar thumb arthritis.

In a healthy carpometacarpal (CMC) or basilar joint of the thumb, the ends of the bones are covered by articular cartilage, thereby providing a natural cushion from compressive forces and are lubricated and nourished by joint (synovial) fluid secreted by specialized cells lining the joint capsule. When a patient suffers from arthritis of the thumb CMC or basilar joint, the cartilage degrades and the relationship between adjacent or opposing bones is no longer protected from compressive and shear forces by the healthy cartilage cover. This results in a series of mechanical and biochemical alterations that result in pain, limited motion, instability, and deformity.

Treatment options for CMC or basilar thumb arthritis include, for example, splints (temporary immobilization of the patient's basilar joint), medication, corticosteroid injections, and surgery. Surgical treatments are typically of two general forms: motion-eliminating and motion-sparing options. The motion-eliminating alternative includes an arthrodesis or a fusion of the bones, thus completely sacrificing all motion between two bones through their respective joint surfaces by promoting bone growth across the former articulation.

Motion-sparing treatments may include, for example, simple removal of diseased bones (with or without accompanying soft tissue stabilization procedures) or removal of diseased bones and subsequent replacement (arthroplasty) of certain bones in the affected joint with biologic and non-biologic implants. More particularly, for CMC or basilar joint arthritis of the thumb, the trapezium bone of the patient's basilar joint may be partially removed (subtotal excision) or totally removed (total excision) to relieve the discomfort and mechanical problems associated with arthritis. The void created by either partial or complete excision of the joint shared by the trapezium and metacarpal bones (or other local carpal bones, as described) can then be left in that state or the resulting void can be filled by biologic or non-biologic material, i.e. an arthroplastic implant.

An approach to bone and joint implants is disclosed in U.S. Pat. No. 4,164,793 to Swanson, which discloses a lunate bone implant. The implant includes a body and a stabilizing stem extending therefrom. Another approach is disclosed in U.S. Pat. No. 4,198,712 to Swanson, which discloses a scaphoid bone implant. This implant also includes a body and a stabilizing stem extending therefrom.

An approach to a CMC or basilar joint implant is disclosed in U.S. Pat. No. 5,645,605 to Klawitter. The implant includes a threaded shaft portion for coupling to the first metacarpal bone of the patient's hand, and an articulating portion coupled thereto for replacing the articulating portion of the trapezium bone.

Potential drawbacks to the disclosed basilar joint implants may include, for example, instability of the implant, i.e. the implant may become dislodged. Moreover, the implants may not be mechanically robust and may break down under constant wear and tear within the basilar joint. Moreover, after implantation, the patient may not be provided with the sufficient thumb motion.

More particularly, in basilar joint implants that replace the trapezium bone, the bases of the first and second metacarpal bones may impinge upon one another and cause the patient discomfort. Moreover, the implantation of such an implant may inadvertently change the length of the patient's thumb, i.e. foreshortening and telescoping of the osteo-articular column.

SUMMARY OF THE INVENTION

In view of the foregoing background, it is therefore an object of the present invention to provide a more effective basilar or carpometacarpal (CMC) joint arthroplastic implant for a thumb of a patient.

This and other objects, features, and advantages in accordance with the present invention are provided by an arthroplastic implant for a basilar joint of a hand of the patient. The arthroplastic implant may include a body having a distal surface and a proximal surface opposite therefrom with the distal surface to be positioned adjacent a first metacarpal bone at the basilar joint of the hand of the patient, and a shield extending outwardly from the distal surface of the body to shield adjacent portions of the first metacarpal bone and a second metacarpal bone of the hand of the patient. Advantageously, the arthroplastic implant may prevent impingement of the patient's first and second metacarpal bones.

More specifically, the body may have a disk shape, and the shield may have an arcuate shape. Moreover, the proximal surface of the body may be positioned adjacent a carpal bone. Also, the body may have rounded over corner portions. The body may have a sidewall with a peripheral medial recess therein. The shield may extend between one quarter to three quarters of a distance around a periphery of the body. The body and the shield may be integrally formed as a monolithic unit.

In some embodiments, the body may include at least one fastener-receiving passageway extending therethrough or a plurality thereof having different diameters. The distal surface may have one of a planar shape, a convex shaper and a concave shape, for example. Additionally, the proximal surface may have one of a planar shape, a convex shape, and a concave shape, for example.

In other embodiments, the arthroplastic implant may further comprise an anchor peg extending outwardly from the body. More particularly, the anchor peg may a tapered shaped. Also, the anchor peg may have a textured surface. The anchor peg may further have a flexible expandable end.

Another aspect is directed to a method of making an arthroplastic implant for a basilar joint of a hand of a patient. The method may include forming a body having a distal surface and a proximal surface opposite therefrom with the distal surface to be positioned adjacent a first metacarpal bone at the basilar joint of the hand of the patient, and forming a shield extending outwardly from the distal surface of the body to shield adjacent portions of the first metacarpal bone and a second metacarpal bone of the hand of the patient.

Yet another aspect is directed to a method of implanting an arthroplastic implant for a basilar joint of a hand of a patient. The method may include providing the arthroplastic implant. The arthroplastic implant may include a body having a distal surface and a proximal surface opposite therefrom with the distal surface to be positioned adjacent a first metacarpal bone at the basilar joint of the hand of the patient, and a shield extending outwardly from the distal surface of the body to shield adjacent portions of the first metacarpal bone and a second metacarpal bone of the hand of the patient. The method may also include implanting the arthroplastic implant into the basilar joint of the hand of the patient.

BRIEF DESCRIPTION OF THE DRAWINGS

FIG. 1 is a perspective view of an arthroplastic implant according to the invention.

FIG. 2 is a side elevational view of the arthroplastic implant of FIG. 1.

FIG. 3 is a backside elevational view of the arthroplastic implant of FIG. 1.

FIG. 4 is a top plan view of the arthroplastic implant of FIG. 1.

FIG. 5 is a cross-sectional view taken along the lines 5-5 of FIG. 3.

FIG. 6 is a cross-sectional view taken along the lines 6-6 of FIG. 2.

FIG. 7 is a perspective view of another embodiment of the arthroplastic implant according to the invention.

FIG. 8 is a perspective view of yet another embodiment of the arthroplastic implant according to the invention.

FIG. 9 is a top plan view of the arthroplastic implant of FIG. 8.

FIG. 10 is a side elevational view of the arthroplastic implant of FIG. 8.

DETAILED DESCRIPTION OF THE PREFERRED EMBODIMENTS

Figure 12:
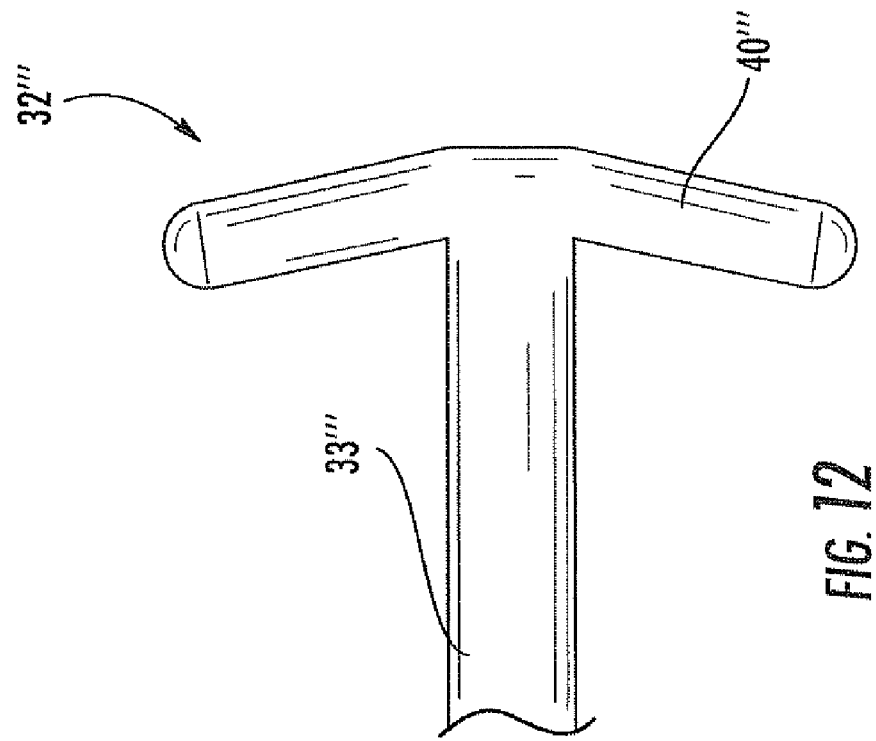
FIG. 12 is a side elevational view of another embodiment of the anchor peg of the arthroplastic implant according to the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and multiple prime notation is used to indicate similar elements in alternative embodiments.

Referring to FIGS. 1-6, an arthroplastic implant 20 for a basilar or carpometacarpal (CMC) joint of a hand of a patient is now described. As will be appreciated by those skilled in the art, the arthroplastic implant 20 is a motion sparing type implant. The arthroplastic implant 20 may be used to treat the development of Osteoarthritis, or other forms of joint pathology, in the basilar joint of the patient. Nonetheless, and as will be appreciated by those skilled in the art, the arthroplastic implant 20 may be used to treat other conditions were arthroplastic surgery is desirable, for example, posttraumatic arthritis.

The arthroplastic implant 20 illustratively includes a body 21 having a distal surface 23 and a proximal surface 24 opposite therefrom. Once surgically implanted into the basilar joint of the patient, the distal surface 23 is to be positioned adjacent a first metacarpal bone at the basilar joint of the hand of the patient, more particularly, the proximal extent of the first metacarpal bone, and the proximal surface 24 is to be positioned adjacent either the scaphoid bone, the trapezium bone, or a portion thereof, i.e. carpal bones. In other words, and as will be appreciated by those skilled in the art, the arthroplastic implant 20 may replace (total excision) the trapezium bone of the basilar joint or supplement the trapezium bone (retention or subtotal excision of the trapezium bone) by being interposed between a trapezial remnant (retained trapezium) and the proximal extent of the patient's first metacarpal.

More specifically, the body 21 illustratively includes a disk shape and has rounded over corner (edge) portions 25. The body 21 illustratively includes a sidewall 27 with a peripheral medial recess therein. Furthermore, the arthroplastic implant 20 illustratively comprises a dielectric material, but may alternatively comprise at least one of the following materials: hydrogel (silicone or polyvinyl alcohols), metal (stainless steel or titanium), biologics (collagen or other organic materials), ceramics (pyrolytic carbon), and polymers (polyethylene), for example. Moreover, in some embodiments, the arthroplastic implant 20 may comprise a combination of metal and the orthopedic hydrogel.

The arthroplastic implant 20 also includes a shield 22, which illustratively has an arcuate (convex towards the second metacarpal bone and concave towards the first metacarpal bone) shape, extending outwardly from the distal surface 23 of the body 21 to shield adjacent portions of the first metacarpal bone and a second metacarpal bone of the hand of the patient. In other words, the shield 22 may serve as an interposed "bumper" between the first two rays of the patient's hand, with the convex side of the shield 22 facing the ulnar side of the patient's wrist, and the concave side of the shield 22 facing the radial side of the patient's hand. The body 21 and the shield 22 may be integrally formed as a monolithic unit, thereby reducing sites of potential mechanical failure, manufacturing costs, and complexity.

In some embodiments, the shield 22 may have a near planar shape, i.e. a gentle curvature, since the articular surfaces of the second metacarpal and the trapezoid bones are near flat. Moreover, this gentle curvature of the arthroplastic implant 20 may advantageously cradle the base of the first metacarpal bone. In other embodiments, the radius of curvature of the shield 22 may be greater in order to better accommodate or fit individual anatomic variations in this region of the patient's hand and wrist.

Advantageously, the arthroplastic implant 20 may prevent impingement of the patient's first and second metacarpal bones after implantation, thereby reducing the patient's post surgical implantation discomfort. Moreover, the shield 22 also assists in properly positioning the arthroplastic implant 20 in the basilar joint of the patient, i.e. improved stability. Moreover, the thickness of the body 21 of the arthroplastic implant 20 may maintain near normal length of osteo-articular column of the thumb, even after complete or partial removal of the trapezium bone, thus preventing foreshortening of the thumb ray. The shield 22 may extend between one quarter to three quarters of a distance around a periphery of the body 21. As will be appreciated by those skilled in the art, the length of the shield 22 may vary based upon the native anatomy of the patient.

The body 21 illustratively includes a plurality of fastener-receiving passageways 26a-26c extending therethrough and illustratively being parallel to the distal and proximal surfaces 23, 24. As will be appreciated by those skilled in the art, the fastener-receiving passageways 26a-26c may receive, for example, a slip of tendon (extensor carpi radialis longus (ECRL) or flexor carpi radialis (FCR) muscles or free graft, for example), sutures of an anchor secured to the base of the second metacarpal bone or the trapezoid bone, or a screw. As will be appreciated by those skilled in the art, the choice of anchoring of the arthroplastic implant 20 may be based upon access available by the native anatomy of the patient and/or the amount of excision for the trapezium bone. Furthermore, some embodiments (not shown) of the arthroplastic implant 20 may not include the fastener-receiving passageways, but may alternatively include another fastener or anchor.

The distal surface 23 illustratively includes a slight concave shape but may alternatively have one or more of a planar shape, a convex shape, or a contoured shape to reflect local anatomy, for example. As will be appreciated by those skilled in the art, the shape of the distal surface 23 may be varied to more accurate fit the base of the first metacarpal bone. Additionally, the proximal surface 24 also illustratively includes a concave shape but may alternatively have one or more of a planar shape, a convex shape, or a contoured shape to reflect local anatomy, for example. As will also be appreciated by those skilled in the art, the shape of the proximal surface 24 may be varied to more accurate fit either the distal pole of the scaphoid bone (total excision) or the remaining portion of the trapezium bone (subtotal excision). Furthermore, the thickness of the body 21 of the arthroplastic implant 20 (the distance between the proximal 24 and distal 23 surfaces) may be variable and permit choices for optimizing the match between the arthroplastic implant and the patient's individual anatomy.

Furthermore, in some embodiments, not shown, the arthroplastic implant 20 may include a projection or stem of one of several geometric shapes and lengths from this distal surface 23 to be inserted into the medullary canal of the first metacarpal so prepared to accept an implant.

Referring now to FIG. 7, another embodiment of the arthroplastic implant 20' is now described. In this embodiment of the arthroplastic implant 20', those elements already discussed above with respect to FIGS. 1-6 are given prime notation and most require no further discussion herein. This embodiment differs from the previous embodiment in that the arthroplastic implant 20' includes only one fastener-receiving passageway 26'. Moreover, the body 21' does not include a sidewall with a peripheral medial recess.

Referring again to FIGS. 1-6, another aspect is directed to a method of making an arthroplastic implant 20 for a basilar joint of a hand of a patient. The method may include forming a body 21 having a distal surface 23 and a proximal surface 24 opposite therefrom with the distal surface to be positioned adjacent a first metacarpal bone at the basilar joint of the hand of the patient, and forming a shield 22 having an arcuate shape, in the illustrated embodiment, and extending outwardly from the distal surface of the body to shield adjacent portions of the first metacarpal bone and a second metacarpal bone of the hand of the patient.

Yet another aspect is directed to a method of implanting an arthroplastic implant 20 for a basilar joint of a hand of a patient. The method may include providing the arthroplastic implant 20. The arthroplastic implant 20 may include a body 21 having a distal surface 23 and a proximal surface 24 opposite therefrom with the distal surface to be positioned adjacent a first metacarpal bone at the basilar joint of the hand of the patient, and a shield 22 having an arcuate shape and extending outwardly from the distal surface of the body to shield adjacent portions of the first metacarpal bone and a second metacarpal bone of the hand of the patient. The method may also include implanting the arthroplastic implant 20 into the basilar joint of the hand of the patient.

Referring to FIGS. 8-10, another arthroplastic implant 30 for a basilar joint of a hand of a patient illustratively includes a body 35 having a distal surface 31 and a proximal surface 36 opposite therefrom. After implantation into the basilar joint of the hand of the patient, the distal surface 31 would be positioned adjacent a first metacarpal bone. As with the arthroplastic implant 20 described above, this arthroplastic implant 30 may replace (total excision) the trapezium bone of the basilar joint or supplement the trapezium bone (subtotal excision and non-trapezial excision).

The arthroplastic implant 30 illustratively includes an anchor peg 32 extending outwardly from the body 35 to anchor the body within the basilar joint of the hand of the patient. Also, the body 35 illustratively includes a disk shape and rounded over corner (edge) portions 34. Advantageously, the arthroplastic implant 30 may be accurately implanted into the basilar joint of the patient. For example, the anchor peg 32 may be coupled to a pre-drilled opening in an adjacent basilar joint bone (proximal first and second metacarpal bone or trapezoid bone) or a screw may be threaded through the anchor peg into the same bones.

The anchor peg 32 illustratively includes a tapered shaped, i.e. the diameter of the anchor peg reduces as it extends from the body 35. The anchor peg 32 also illustratively includes a textured surface 33, for example, the illustrated ribbed surface, a screw (threaded) surface, a smooth surface, a porous surface, or a rough surface.

Additionally, the body 35 and the anchor peg 32 may be integrally formed as a monolithic unit. In other embodiments (FIG. 11), the arthroplastic implant 30 may further comprise a band carrying the anchor peg 32 and positioned to surround the body 35 to thereby join the anchor peg to the body.

As with the arthroplastic implant 20 described above, this arthroplastic implant 30 illustratively includes convex distal and proximal surfaces 31, 36, but the shape of the distal surface 31 may be varied to more accurately fit the base of the first metacarpal bone. Additionally, the shape of the proximal surface 31 may be varied to more accurately fit either the distal pole of the scaphoid bone (total excision) or the remaining portion of the trapezium bone (subtotal or partial excision).

Referring now to FIGS. 1-6 and 8-10, as with the arthroplastic implant 20 described above, this arthroplastic implant 30 may also include a shield having an arcuate shape and extending outwardly from the distal surface 31 of the body 35 to shield adjacent portions of the first metacarpal bone and a second metacarpal bone of the hand of the patient.

Moreover, as also will be appreciated by those skilled in the art, in embodiments of the arthroplastic implant 20 described above that do not include fastener-receiving passageways 26a-26c, the arthroplastic implant 20 may advantageously further comprise an anchor peg extending outwardly from the body. As will be appreciated by those skilled in the art, in certain embodiments, the arthroplastic implants 20, 30 described herein may include one or more of the shield, the anchor peg feature, and the fastener-receiving passageways for greater stabilization.

Figure 11:
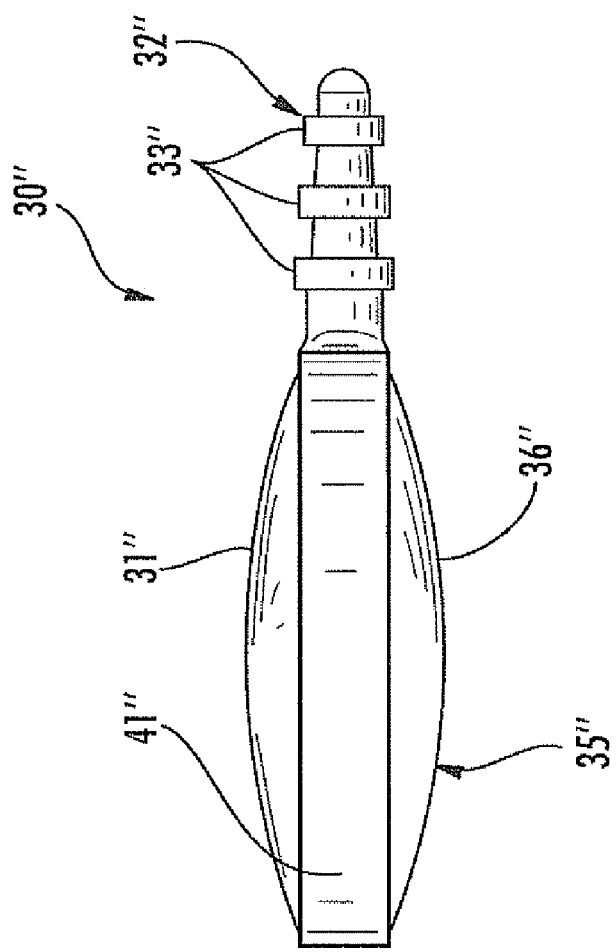
FIG. 11 is a side elevational view of another embodiment of the arthroplastic implant according to the invention.

Referring now to FIG. 11, another embodiment of the arthroplastic implant 30" is now described. In this embodiment of the arthroplastic implant 30", those elements already discussed above with respect to FIGS. 8-10 are given double prime notation and most require no further discussion herein. This embodiment differs from the previous embodiment in that the arthroplastic implant 30" further comprises a band 41" carrying the anchor peg 32" and positioned to surround the body 35" to thereby join the anchor peg to the body, i.e. the arthroplastic implant 30" is not monolithic.

Referring now to FIG. 12, another embodiment of the arthroplastic implant 30'" is now described. In this embodiment of the arthroplastic implant 30'", those elements already discussed above with respect to FIGS. 8-10 are given triple prime notation and most require no further discussion herein. This embodiment differs from the previous embodiment in that the anchor peg 32'" illustratively includes a flexible expandable end 40'". Moreover, the flexible expandable end 40'" of the anchor peg 32'" has an enlarged size for aiding in anchoring the body 35'". For example, an opening may be pre-drilled into an adjacent basilar joint bone, and the enlarged flexible expandable end of the anchor peg 32'" may be compressed to fit through the opening and thereafter expand within the intramedullary portion of the bone, thereby anchoring the arthroplastic implant 30'".

Referring again to FIGS. 8-10, another aspect is directed to a method of making an arthroplastic implant 30 for a basilar joint of a hand of a patient. The method may include forming a body 35 having a distal surface 31 and a proximal surface 36 opposite therefrom with the distal surface to be positioned adjacent a first metacarpal bone at the basilar joint of the hand of the patient, and forming an anchor peg 32 extending outwardly from the body to position the body within the basilar joint of the hand of the patient.

Yet another aspect is directed to a method of implanting an arthroplastic implant 30 for a basilar joint of a hand of a patient. The method may include providing the arthroplastic implant 30. The arthroplastic implant 30 may include a body 35 having a distal surface 31 and a proximal surface 36 opposite therefrom with the distal surface to be positioned adjacent a first metacarpal bone at the basilar joint of the hand of the patient, and an anchor peg extending outwardly from the body to position the body within the basilar joint of the hand of the patient. The method may also include implanting the arthroplastic implant into the basilar joint of the hand of the patient.

Other features relating to implants are disclosed in copending applications "MODULAR BONE FIXATION DEVICE FOR TREATMENT OF FRACTURES AND RELATED METHODS", Attorney Docket No. 60282; "ARTHRODESIS IMPLANT FOR FINGER JOINTS AND RELATED METHODS", Attorney Docket No. 60284; and "ARTHROPLASTIC IMPLANT WITH ANCHOR PEG FOR BASILAR JOINT AND RELATED METHODS", Attorney Docket No. 60285, all incorporated herein by reference in their entirety.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An arthroplastic implant for a basilar joint of a hand of a patient comprising:
   a body having a distal surface and a proximal surface opposite therefrom with the distal surface to be positioned adjacent a first metacarpal bone at the basilar joint of the hand of the patient; and
   a shield rigidly connected to said body and having an arcuate shape extending outwardly from the distal surface of said body, said shield extending between about one quarter to about three quarters of a distance around a periphery of said body to shield adjacent portions of the first metacarpal bone and a second metacarpal bone of the hand of the patient.

2. The arthroplastic implant according to claim 1 wherein the proximal surface of said body is configured and arranged to engage a carpal bone.

3. The arthroplastic implant according to claim 1 wherein said body has rounded over corner portions.

4. The arthroplastic implant according to claim 1 wherein said body has a sidewall with a peripheral medial recess therein.

5. The arthroplastic implant according to claim 1 wherein said body has at least one fastener-receiving passageway extending entirely therethrough.

6. The arthroplastic implant according to claim 5 wherein said at least one fastener-receiving passageway comprises a plurality thereof having different diameters.

7. The arthroplastic implant according to claim 1 wherein the distal surface has one of a planar shape, a convex shape, and a concave shape.

8. The arthroplastic implant according to claim 1 wherein the proximal surface has one of a planar shape, a convex shape, and a concave shape.

9. The arthroplastic implant according to claim 1 further comprising an anchor peg extending outwardly from said body.

10. The arthroplastic implant according to claim 9 wherein said anchor peg has a tapered shape.

11. The arthroplastic implant according to claim 9 wherein said anchor peg has a textured surface.

12. The arthroplastic implant according to claim 9 wherein said anchor peg has a flexible expandable end that has a collapsed condition prior to being anchored within the basilar joint and an expanded condition when said anchor peg is anchored within the basilar joint.

13. The arthroplastic implant according to claim 1 wherein said body and said shield are integrally formed as a monolithic unit.

14. The arthroplastic implant according to claim 1 wherein the proximal surface of said body is configured and arranged to engage a carpal bone.

15. The arthroplastic implant according to claim 1 wherein said distal surface and said proximal surface have the same shape.

16. The arthroplastic implant according to claim 1 wherein a first side of said shield has a convex shape and a second side of said shield opposite said first side has a concave shape.

17. The arthroplastic implant according to claim 1 wherein a first side of said shield and a second side of said shield opposite said first side have a substantially planar shape.

18. The arthroplastic implant according to claim 1 wherein only one shield extends from said distal surface.

19. An arthroplastic implant for a basilar joint of a hand of a patient comprising:
- a disk-shaped body having a distal surface, a proximal surface opposite therefrom with the distal surface to be positioned adjacent a first metacarpal bone at the basilar joint of the hand of the patient, and at least one fastener-receiving passageway extending through the body and spaced from the distal surface and the proximal surface; and
- a shield having an arcuate shape and extending outwardly from the distal surface of said disk-shaped body, said shield extending between about one quarter to about three quarters of a distance around a periphery of said body to shield adjacent portions of the first metacarpal bone and a second metacarpal bone of the hand of the patient.

20. The arthroplastic implant according to claim 19 wherein said disk-shaped body has rounded over corner portions.

21. The arthroplastic implant according to claim 19 wherein said disk-shaped body has a sidewall with a peripheral medial recess therein.

22. The arthroplastic implant according to claim 19 further comprising an anchor peg extending outwardly from said disk-shaped body.

23. The arthroplastic implant according to claim 22 wherein said anchor peg has a tapered shaped.

24. The arthroplastic implant according to claim 19 wherein said distal surface and said proximal surface have the same shape.

25. The arthroplastic implant according to claim 19 wherein a first side of said shield has a convex shape and a second side of said shield opposite said first side has a concave shape.

26. The arthroplastic implant according to claim 19 wherein a first side of said shield and a second side of said shield opposite said first side have a substantially planar shape.

27. The arthroplastic implant according to claim 19 wherein only one shield extends from said distal surface.

28. An arthoplastic implant for a basilar joint of a hand of a patient comprising:
- a disk-shaped body having a distal surface for engaging a first metacarpal bone of the hand of the patient and a proximal surface opposite the distal surface for engaging a carpal bone of the hand of the patient; and
- a shield integrally formed with the body and extending from the distal surface of the body for shielding adjacent portions of the first metacarpal bone and a second metacarpal bone of the patient.

29. The arthroplastic implant according to claim 28 wherein said distal surface and said proximal surface have the same shape.

30. The arthroplastic implant according to claim 28 wherein a first side of said shield adjacent the second metacarpal bone has a convex shape and a second side of said shield opposite said first side and adjacent the first metacarpal bone has a concave shape.

31. The arthroplastic implant according to claim 28 wherein a first side of said shield and a second side of said shield opposite said first side have a substantially planar shape.

32. The arthroplastic implant according to claim 28 wherein only one shield extends from said distal surface.

* * * * *